United States Patent [19]

Cambon et al.

[11] 3,965,092

[45] June 22, 1976

[54] PERFLUOROALKYL BENZODIAZEPINES

[75] Inventors: Aimé Cambon, Nice; Claude Giovannoni, Salindres; Raphaël Pastor; Jean Riess, both of Nice, all of France

[73] Assignee: Produits Chimiques Ugine Kuhlmann, Paris, France

[22] Filed: May 21, 1974

[21] Appl. No.: 471,837

[30] Foreign Application Priority Data

May 22, 1973 France .............................. 73.18488

[52] U.S. Cl. ........................... 260/239 BD; 252/78; 252/357; 260/575; 260/578; 260/592; 260/593 H
[51] Int. Cl.² ..................................... C07D 243/12
[58] Field of Search .............................. 260/239 BD

[56] References Cited

OTHER PUBLICATIONS

Becker, Chem. Abstracts, vol. 44, Col. 1029–1030 (1950).
Barltrop et al., J. Chem. Soc., (London), 1959, pp. 1132–1142.
Archer et al., Chem. Reviews, vol. 68, p. 771 (1968).

*Primary Examiner*—Alton D. Rollins
*Attorney, Agent, or Firm*—Pennie & Edmonds

[57] ABSTRACT

New perfluoroalkyl derivatives of benzodiazepine are prepared by reacting an orthophenylenediamine with a beta-diketone at least one of whose alkyls is a $C_1$ – $C_{15}$ perfluoroalkyl. The stable products are useful as heat-exchange substances and as surfactants in organic solution.

2 Claims, No Drawings

3,965,092

PERFLUOROALKYL BENZODIAZEPINES

BACKGROUND OF THE INVENTION

Substituted 1,5-benzodiazepines are known having the formula

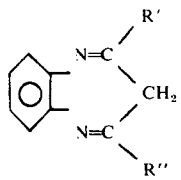

wherein R' and R'' are hydrocarbon radicals, as reported, for example, by Barltrop et al, J. Chem. Soc. 1959 p. 1132. Their synthesis by reaction of o-phenylene diamine with beta-diketones was reported by Thiele and Steimmig, Ber. 40 955 (1907). To the best knowledge of present inventors, benzodiazepines substituted by fluorinated radicals, in particular by perfluorinated radicals, have not been disclosed.

SUMMARY OF THE INVENTION

The present invention provides new benzodiazepines substituted by one or two perfluoroalkyl groups. In these new benzodiazepines, either one or both of the groups R' and R'' in the above formula can be a perfluoroalkyl group. The new compounds have unique properties resulting from the lyophilic balance obtainable with the perfluorinated groups and are thus useful as surfactants in organic solution. Their high rates of transmitting heat make them ideal substances for heat exchange media, their stability at high temperature being surprising in view of the disclosure in the Barltrop reference (page 1133 line 2) that benzodiazepines are an unstable system.

Briefly stated, this invention relates to a perfluoroalkylated benzodiazepine having the formula

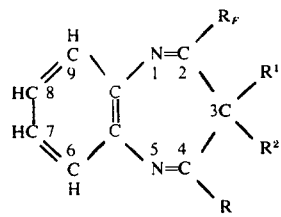

wherein $R_F$ is a $C_1 - C_{15}$ perfluoroalkyl group and R is the same as $R_F$ or a different $C_1 - C_{15}$ perfluoroalkyl group or a phenyl group or a phenyl group substituted by a $C_1 - C_4$ alkyl group; wherein $R^1$ and $R^2$, the same or different, are H or $C_1 - C_5$ alkyl or Br or Cl; and wherein the benzene ring, in positions 6, 7, 8 and 9, is unsubstituted or substituted by one or more groups which are $C_1 - C_4$ alkyl or nitro (—$NO_2$), methoxy (—$OCH_3$), hydroxy (—OH), amino (—$NH_2$), chlorine (—Cl) or bromine (—Br).

This invention relates also to a method of making the new perfluoroalkylated benzodiazepines which comprises reacting, in a solvent containing at least one $C_1 - C_4$ aliphatic alcohol or water or mixtures of water-alcohols and in the presence of a catalytic amount of an acid, an orthophenylene diamine with a beta-diketone

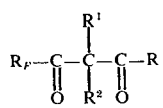

wherein $R_F$, R, $R^1$ and $R^2$ have the same meanings as above stated and wherein the benzene ring of the phenylene diamine is either unsubstituted in the 3, 4, 5 and 6 positions or substituted by one or more groups which are $C_1 - C_4$ alkyl, or nitro, methoxy, hydroxy, amino, chlorine or bromine.

This invention also relates to the uses of the new perfluoroalkylated benzodiazepines as heat-exchange fluids and as surfactants in organic solutions.

DETAILED DESCRIPTION

The perfluorinated alkyl group $R_F$ which is substituted in the 2-position, optionally also in the 4-position, of the benzodiazepines of this invention is any straight chain, branched or cyclic alkyl group having from 1 to 15 carbon atoms and having substantially all of its hydrogens replaced by fluorine. Exemplarily, said perfluoroalkyl group is trifluoromethyl, pentafluoroethyl, heptafluoro-n-propyl, heptafluoroisopropyl, nonafluoro-n-butyl, nonafluoroisobutyl, nonafluoro-secondary butyl, nonafluoro-tertiary butyl, undecafluoro-n-amyl, undecafluoro-isoamyl, undecafluoro-tertiary amyl, tridecafluoro-n-hexyl, undecafluoro-cyclohexyl, pentadecafluoroheptyl, heptadecafluoro octyl, heptadecafluoro-2-ethylhexyl, nonadecafluorononyl, perfluorodecyl ($C_{10}F_{21}$), perfluoroundecyl ($C_{11}F_{23}$), perfluorolauryl ($C_{12}F_{25}$), perfluoromyristyl ($C_{14}F_{29}$), perfluorotridecyl ($C_{13}F_{27}$), perfluoropentadecyl ($C_{15}F_{31}$) and the like. The preferred perfluoroalkyl groups $R_F$ are heptafluoro propyl, undecafluoro amyl and pentadecafluoro heptyl.

The second substituent R in the benzodiazepine of this invention can also be a group $R_F$ as enumerated above, being either the same or a different $R_F$ or it can be phenyl or a phenyl substituted in any place on the ring by a $C_1 - C_4$ alkyl group. This R can exemplarily be o-tolyl, p-tolyl, m-tolyl, o-xylyl, p-xylyl, m-xylyl, o-ethylphenyl, m-isopropylphenyl, p-propylphenyl, p-butylphenyl, m-butyl p methyl phenyl and the like. The preferred R is phenyl or the group $R_F$.

The benzene ring attached to the nitrogens of the instant benzodiazepine can be otherwise unsubstituted, or any one or more of the remaining hydrogens on the ring can be substituted by a $C_1 - C_4$ alkyl group or by certain other substituting groups as herein stated. Thus any of the hydrogens in the 6, 7, 8 and 9 positions can be substituted by, exemplarily, methyl, ethyl, isopropyl, n-propyl, n-butyl, isobutyl, secondary butyl or tertiary butyl, or by nitro (—$NO_2$), methoxy (—$OCH_3$), hydroxy (—OH), amino (—$NH_2$), chlorine (—Cl) or bromine (—Br).

The preferred method of preparing the benzodiazdpines of this invention comprises reacting o-phenyldiamine or a substituted o-phenylenediamine with a beta-ketone having the desired groups $R_F$ and R. Thus, exemplarily,

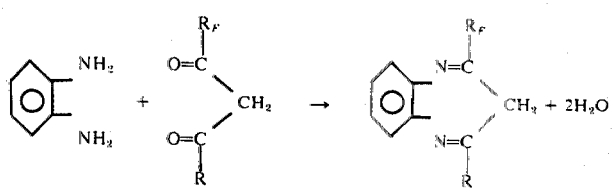

The benzene ring of the diphenylene diamine can be unsubstituted or substituted to correspond to the desired substitution in the benzodiazepine. Thus when, exemplarily, a benzodiazepine is desired having a methyl in the 7-position, the starting diphenylene diamine would be 1,2-diamino-4-methylbenzene. Thus the benzene ring of the phenylene diamine is either unsubstituted in the 3, 4, 5 and 6 positions or substituted at those positions by one or more $C_1 - C_4$ alkyl groups, or by nitro, methoxy, hydroxy, amino, chlorine or bromine.

The reaction can conveniently be carried out in a suitable solvent. The preferred solvents are $C_1 - C_4$ aliphatic alcohols, namely methanol, ethanol n-propanol, isopropanol, butyl alcohol, or water, or mixtures water-alcohols. In general, ethanol, water or the mixtures of water-ethanol are the most preferred solvent.

The reaction between the appropriate o-phenylene diamine and beta-ketone can proceed satisfactorily over a wide range of temperature. In general, it is preferred to allow the dissolved reactants to react at ambient temperatures say 10°–30°C, more preferably 15°–25°C, for a period of at least about 24 hours, preferably for at least 48 hours in a neutral or slightly acide medium. A strong acid like hydrochloric or sulfonic acid may be employed till a pH of about 4. The relatively low temperature leads to good yields.

In contacting the reactants, either the phenylenediamine or the diketone can be used in excess over the stoichiometric amount. Thus from 1 to 2 moles of phenylenediamine can be used with from 2 to 1 moles of diketone. It is preferred to use amounts such that the diketone is in about 20 % excess over stoichiometric. Either reactant can be added gradually to the other, or the reactants can be simply mixed and allowed to react.

After reaction under the stated conditions, a solid precipitate generally has precipitated, usually having a brown color attributable to the presence of unreacted orthophenylenediamine. This solid is separated in a conventional manner from the reaction mixture as, for example, by filtration or centrifugation. Recrystallization of the residue, exemplarily from methanol or ethanol, yields a solid substance having a definite melting point and identifiable as the particular perfluorinated benzodiazepine by chemical analysis and by the various spectra, in particular infra red and nuclear magnetic resonance spectra.

The beta-diketones which are used in carrying out this invention can be prepared by perfluoroacylation of appropriate ketones by esters or acid chlorides of perfluorocarboxylic acids, as in the reaction of methyl perfluorocaprylate with methyl tertiary butyl ketone to make 1-perfluoroheptyl-3 tertiary butyl-1,3 propanedione. Or a methyl perfluoroalkyl ketone can be acylated by an appropriate carboxylic derivative, as in the reaction of methyl phenylacetate with methyl perfluoropentyl ketone to give 1-perfluoropentyl-3-phenyl-1,3-propanedione, or in order to have two perfluorinated groups in the eventual benzodiazepine, a methyl ketone containing also a perfluoroalkyl group can be acylated by an ester of a perfluorinated carboxylic acid as when methyl fluorocaprylate is reacted with methyl perfluoroheptyl ketone to produce 1,3-di-(perfluoroheptyl)-1,3-propanedione.

Among the beta-diketones which can be used in the present invention, some having polyfluorinated lower alkyl groups are known as disclosed, for example, in R. A. MOORE and R. LEVINE J. ORG. CHEM. 29 page 1439 (1964). Others have been synthesized for the first time by present inventors.

When it is desired to have $R^1$ and/or $R^2$ be other than H, the hydrogens in the 2-position of the propanedione can be easily replaced by an alkyl group; particularly by a $C_1 - C_5$ alkyl group, by reaction with sodium amide and the appropriate alkyl iodide. Thus, for example, 1-n-perfluoropentyl-3-phenyl-1,3-propanedione can be reacted with one mole each of $NaNH_2$ and $C_2H_5I$ to produce 1-n-perfluoropentyl-2-ethyl-3-phenyl-1,3-propanedione; or with 2 moles each of $NaNH_2$ and $C_2H_5I$ to produce 1-n-perfluoropentyl-2,2-diethyl-3-phenyl-1,3-propanedione. Or 1-n-pentadecafluoroheptyl-3-phenyl-1,3-propanedione can be reacted with 2 moles $NaNH_2$, 1 mole of $CH_3I$ and 1 mole n-$C_5H_{11}I$ to produce 1-n-pentadecafluoroheptyl-2-methyl-2-ethyl-3-phenyl-1,3-propanedione.

Alternatively, the said alkyls can be substituted for the hydrogen atom after the condensation with the orthodiphenylenediamine has taken place, namely the sodium amide and alkyl iodide can be reacted with the benzodiazepine having an hydrogen atom in the 3-position.

The ease of replacing said hydrogen atom is attributable to their extreme mobility characteristic of their "malonic" position.

$R^1$ and $R^2$ can be replaced also by bromine or chlorine by conventional halogenation either before or after condensation to the benzodiazepine.

EXAMPLE 1

Preparation of 2-n-perfluoropentyl-4-phenyl-1,5-benzodiazepine.

Into 80 cc. of ethyl alcohol, there were placed 0.01 mol (1.08 grams) of orthophenylenediamine and 0.012 mol (5.04 grams) of 1-n-perfluoropentyl-3-phenyl-1,3-propanedione, otherwise designated as 1,1,1,2,2,3,3,4,4,5,5-undecafluoro-7-benzoyl-6-heptanone. The solution was acidified by addition of 1 cc. of glacial acetic acid and agitated over a period of 48 hours at ambiant temperature (20°–25°C).

A precipitate was formed. This was filtered off and recrystallized from carbon tetrachloride as 3.5 grams of a solid melting at 86°C and corresponding to a 70 % yield of a compound whose analysis, given below, and infra-red spectrum, nuclear magnetic resonance spectrum, mass-spectrum and ultra-violet spectrum all indicated to have the structure

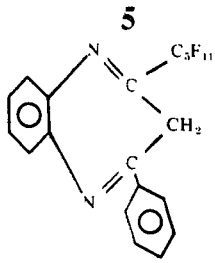

| QUANTITATIVE ANALYSIS | | |
|---|---|---|
| | Calc'd for $C_{20}H_{11}N_2F_{11}$ | Found |
| % Carbon | 49.18 | 49.3 |
| % Hydrogen | 2.25 | 2.18 |
| % Nitrogen | 5.74 | 5.67 |
| % Fluorine | 42.83 | 42.85 |

EXAMPLE 2

The procedure of Example 1 was followed in a series of three preparations in which orthophenylenediamine was reacted respectively with:

a. 1-trifluoromethyl-3-phenyl-1,3-propanedione
b. 1-n-heptafluoropropyl-3-phenyl-1,3-propanedione
c. 1-n-pentadecafluoroheptyl-3-phenyl-1,3-propanedione
d. 1-n-undecafluoropentyl-3-phenyl-1,3-propanedione.

The resulting compounds, after recrystallization, melted respectively at (a) 80°C, (b) 98°C and (c) 102°C and the results of quantitative chemical analysis and the various spectra mentioned in Example 1 were in agreement with the formula

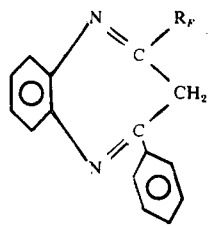

wherein $R_F$ was respectively

| | Yield % |
|---|---|
| (a) $CF_3$ | 89 % |
| (b) $C_3F_7$ | 75 % |
| (c) $C_7F_{15}$ | 46 % |
| (d) $C_5F_{11}$ (melting point 86°C) | 60 % |

EXAMPLE 3

The procedure of Example 1 was followed in a series of three preparations in which 1,2-diamino-4-methyl benzene was reacted respectively with a. 1-n-heptafluoropropyl-3-phenyl-1,3-propanedione
b. 1-n-undecafluoropentyl-3-phenyl-1,3-propanedione
c. 1-n-pentadecafluoroheptyl-3-phenyl-1,3-propanedione The resulting compounds, after recrystallization, melted respectively at (a) 97°C (b) 80°–81°C and (c) 85°–86°C and the results of quantitative chemical analysis and the various spectra were in agreement with the formula

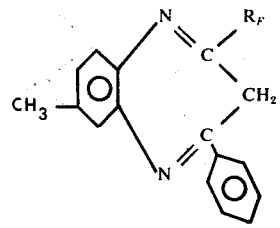

wherein $R_F$ was respectively

| | Yield % |
|---|---|
| (a) $C_3F_7$ | 50 |
| (b) $C_5F_{11}$ | 58 |
| (c) $C_7F_{15}$ | 38 |

EXAMPLE 4

The procedure of Example 1 was followed in a series of three preparations in which 1,2-diamino-4,5-dimethyl benzene was reacted respectively with the same three beta-diketones used in the preparations of Example 3.

The resulting compounds, after recrystallization, melted respectively at (a) 120°C, (b) 115°C and (c) 107°C. The results of quantitative chemical analysis and the various spectra were in agreement with the formula

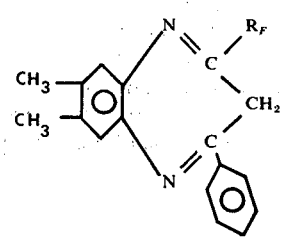

wherein $R_F$ was respectively

| | Yield % | Stable at |
|---|---|---|
| (a) $C_3F_7$ | 82 | 250°C |
| (b) $C_5F_{11}$ | 60 | 250°C |
| (c) $C_7F_{15}$ | 85 | 250°C |

EXAMPLE 5

The procedure of Example 1 was followed in a series of three preparations in which 1,3-di(n-pentadecafluoroheptyl)-1,3-propanedione was reacted with respectively a. o-phenylenediamine
b. 1,2-diamino-4-methyl-benzene
c. 1,2-diamino-4,5-dimethyl benzene The resulting compounds, after recrystallization, melted respectively at (a) 66°C, (b) 63°C and (c) 89°C. The results of quantitative chemical analysis and the various spectra were in agreement with the formula

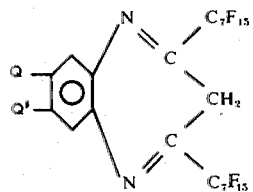

wherein Q and Q' had the following identities

|     | Q   | Q'  | Yield % |
| --- | --- | --- | ------- |
| (a) | H   | H   | 76      |
| (b) | H   | CH₃ | 60      |
| (c) | CH₃ | CH₃ | 85      |

EXAMPLE 6

The procedure of Example 1 is followed in a series of four preparations in which 1-n-pentadecafluoroheptyl-3-phenyl-1,3-propanedione is reacted with respectively
 a. 1,2-diamino-4-ethyl-benzene
 b. 1,2-diamino-4-isopropyl-benzene
 c. 1,2-diamino-4-tertiary-butyl-benzene
 d. 1,2-diamino-4-methyl-5-isobutyl-benzene In each case compounds are obtained which have definite melting points and surfactant properties.

EXAMPLE 7

The procedure of Example 1 is followed in a series of four preparations in which 1-n-perfluorododecyl-3-phenyl-1,3-propanedione is reacted with respectively
 a. 1,2-diamino benzene
 b. 1,2-diamino-4-methyl benzene
 c. 1,2-diamino-4-n-propyl benzene
 d. 1,2-diamino-4-n-butyl-benzene In each case compounds are obtained which have definite melting points and surfactant properties.

EXAMPLE 8

The procedure of Example 1 is followed in a series of four preparations in which 1-n-perfluoropentadecyl-3-phenyl-1,3-propanedione is reacted with respectively
 a. 1,2-diamino benzene
 b. 1,2-diamino-4-methyl benzene
 c. 1,2-diamino-4-n-propyl benzene
 d. 1,2-diamino-4-isobutyl benzene In each case compounds are obtained which have definite melting points and surfactant properties.

EXAMPLE 9

The procedure of Example 1 is followed in a series of six preparations in which 1-n-pentadecafluoroheptyl-3-phenyl-1,3-propanedione is reacted with respectively
 a. 1,2-diamino-4-nitrobenzene
 b. 1,2-diamino-4-methoxybenzene
 c. 1,2-diamino-4-hydroxybenzene
 d. 1,2,4-triamino-benzene
 e. 1,2-diamino-4-chlorobenzene
 f. 1,2-diamino-4-bromobenzene

We claim:

1. A perfluoroalkylated benzodiazepine having the formula

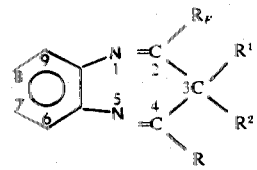

wherein $R_F$ is a $C_1$–$C_{15}$ perfluoro straight chain alkyl group and R is the same as $R_F$ or a different $C_1$–$C_{15}$ perfluoro straight chain alkyl group or a phenyl group or a phenyl group substituted by a $C_1$–$C_4$ alkyl group; wherein $R^1$ and $R^2$ are, independently of each other, hydrogen or $C_1$–$C_5$ alkyl groups; and wherein the benzene ring is unsubstituted in positions 6, 7, 8 and 9 or substituted by a $C_1$–$C_4$ alkyl group in one or both of positions 7 and 8.

2. The perfluoroalkylated benzodiazepine of claim 1 wherein $R^1$ and $R^2$ are H.

* * * * *

UNITED STATES PATENT AND TRADEMARK OFFICE
CERTIFICATE OF CORRECTION

PATENT NO. : 3,965,092
DATED : June 22, 1976
INVENTOR(S) : Aime Cambon et al.

It is certified that error appears in the above-identified patent and that said Letters Patent are hereby corrected as shown below:

Column 2, line 65, change "benzodiazdpines" to

--benzodiazepines--

Column 3, line 36, change "sulfonic" to --sulfuric--

Signed and Sealed this

Twenty-first Day of September 1976

[SEAL]

Attest:

RUTH C. MASON
Attesting Officer

C. MARSHALL DANN
Commissioner of Patents and Trademarks